United States Patent [19]
Lerch

[11] Patent Number: 4,543,828
[45] Date of Patent: Oct. 1, 1985

[54] ULTRASONIC IMAGING SYSTEM

[75] Inventor: Reinhard Lerch, Erlangen, Fed. Rep. of Germany

[73] Assignee: Siemens AG, Berlin and Munich, Fed. Rep. of Germany

[21] Appl. No.: 572,724

[22] Filed: Jan. 20, 1984

[30] Foreign Application Priority Data

Jan. 21, 1983 [DE] Fed. Rep. of Germany ....... 3301981

[51] Int. Cl.⁴ ............................................. G01N 29/00
[52] U.S. Cl. .................................................... 73/626
[58] Field of Search .......................... 73/626, 625, 620; 367/103, 105; 128/660

[56] References Cited

U.S. PATENT DOCUMENTS

| | | | |
|---|---|---|---|
| 4,223,560 | 9/1980 | Glenn | 73/626 |
| 4,241,608 | 12/1980 | Dees et al. | 73/626 |
| 4,417,475 | 11/1983 | Okazaki | 73/626 |
| 4,484,477 | 11/1984 | Buxton | 73/626 |

OTHER PUBLICATIONS

W. Gebhard—"Grundlagen, Technik und Anwendung in der Werkstoffpruefung", IzfP—Bericht Nr. 770117-TW, pp. 60 through 65, Saarbruecken 1977.

*Primary Examiner*—Stephen A. Kreitman
*Attorney, Agent, or Firm*—Thomas H. Jackson

[57]  ABSTRACT

Ultrasonic imaging system with a linear array having several transducer elements of which a respective group of commonly controlled transducer elements forms one beam aperture and to which one transmitting system and one receiving system is allocated. A delay time is digitally set for each transducer element of the beam aperture and triggered by means of a starting pulse. Always only one group of the transducer elements on the linear array is active and is connected via transmit switches to the transmitting system, and via receiver switches in series with a wiring arrangement to the receiving system. This facilitates the implementation of an ultrasonic imaging system for high ultrasonic frequencies, particularly in the order of at least 30 MHz, in which the use of a switching matrix in the radiation and receiving system is avoided.

10 Claims, 3 Drawing Figures

ULTRASONIC IMAGING SYSTEM

BACKGROUND OF THE INVENTION

This invention relates to an ultrasonic imaging system with a linear array consisting of several transducer elements which are divided into groups. Each group of commonly controlled transducer elements forms one beam aperture to which one transmitting system and one receiving system is allocated. Each group is equipped with electronic focusing through phase delay for its sound field and with a parallel scanning of the sound field by electronic advancement.

During non-destructive material testing with ultrasound, focusing modulators are more often used for determining the extent of imperfections because of the improved resolution they provide. However, the modulators require different test probes with appropriate focal distances at different depths of imperfection investigation. Thus substantial savings of testing time and costs can be achieved with the introduction of an array test probe because it permits electronic focusing at different depths of the material.

Systems employing the technique of horizontal rows of transmitters can be roughly divided into three groups, i.e. image converters, actual or real-time scanners and phase-modulated arrays of transmitters or phased arrays.

Image converters are systems in which the image of an object penetrated by sound is pictured on a linear or planar array by means of acoustic lens. The stationary distribution of sound pressure across the plane of the array is scanned by cycling through one element after the other. Since the resolution and the field of view depend on the size and number of the elements, the number of individual elements for image converters becomes relatively large, typically several thousands. The acoustic lens/image converter system, in other words, registers the stationary distribution of the sound pressure in an object plane that is parallel to the array side.

The real-time scanner, on the other hand, operates in the pulse/echo mode. The test probe is a linear array, whose elements are activated one after the other, individually or in groups. From the magnitude of the echo and from the delay time, a B-image is created on an intensity-modulated oscilloscope. The width of the image is determined by the length of the array.

Phased-arrays and their test probe, in contrast to the real-time scanner, generally have a smaller number of elements and all of the individual modulators contribute to the formation and control of the sound field. Because of the sweeping movement of the beam, a relatively large, sector-shaped B-image is obtained with this technique in spite of the shortness of the test probe.

An ultrasonic imaging system for examination of pressurized reactor containers is known as a phase-modulated pulse-echo system which, in addition to A-, B- and C-scans provides the possibility of holographic examinations. The entire system is controlled by a PDP 11/34 computer. The pulse-echo operation is used for rapid error search and localization. The acoustic halography then provides more accurate information concerning areas that are suspect of imperfections. The test probe contains a linear array of 120 transmitting and receiving elements which are arranged in two adjacent rows. The system operates at an ultrasonic frequency of 2.3 MHz and the element spacing is $\lambda/2$ for density waves and $\lambda$ for shear waves. Every element has its own pulse generator. A transmitting and a receiving system is allocated to these transmitting and receiving elements. For pulse-echo operation, 16 of the 120 elements are always combined during the transmitting phase; during the receiving phase, only 8 elements of this group are operating. During the transmitting phase, the beam aperture consists of 16 elements which are connected to the 120 elements by means of a switching matrix. The receive signals are routed via a switching matrix, pre-amplified, converted from analog to digital signals, appropriately delayed by means of a shift register and reconverted to analog signals. The testing speed of welding seams is up to $\frac{1}{2}$ square meter/min (W. Gebhard:—"Grundlagen, Technik und Anwendung in der Werkstoffpruefung", IzfP—Bericht Nr. 770117-TW, pages 60 through 65, Saarbruecken 1977).

In this well-known ultrasonic imaging system, the selection of the array is implemented by means of a switching matrix. However, it does not seem possible to create a switching matrix consisting of several thousands switching matrix points, and which still functions well at high ultrasonic frequencies.

SUMMARY OF THE INVENTION

It is an object of the invention to provide an ultrasonic imaging system for high ultrasonic frequencies, specifically at least approximately 30 MHz, in which the use of a switching matrix in the transmitting receiving system is avoided. Additionally, the ultrasonic imaging system should facilitate the presentation of an ultrasonic C-image of finely-structured objects at this ultrasonic frequency.

It is a further object of the invention to provide an ultrasonic imaging system which is suitable for use in the field of medicine, preferably for the diagnosis of skin diseases (dermatosis) and specifically for diagnosis during open heart surgery.

It is a further object of the invention that the system be suitable for use in non-destructive material testing, primarily in the fault localization of thin, soldered and bonded layers, specifically for determining the thickness of the layers in multilayer systems.

The foregoing objects and others are achieved by the invention having the characteristic features of claim 1. An ultrasonic imaging system for high ultrasonic frequencies, specifically of at least 30 MHz, can be created by digitally setting one delay time for every transducer element of the beam aperture and triggering it by means of a starting pulse. Only one group of the transducer elements of the linear array is active and, in each case, connected to the transmitting system via transmit switches and connected to the receiving system via receiver switches in series with a wiring arrangement. In this ultrasonic imaging system operating in the pulse-echo mode, which, e.g., consists of several, preferably several hundred, of linearily arranged transducer elements, the selection is phase-delayed for the purpose of focusing. In other other words, an ultrasonic lens is created by electronic means. The beam aperture, which consists, e.g., of several, preferably approximately 15 and specifically, approximately 30, linearily arranged transducer elements, is advanced electronically. For instance, by using group advancement, preferably by using the half-cycle method and specifically, by using a modified half-cycle method and the electronic advancing is achieved.

By implementing these features of the functions of several individual test probes used in the design can be combined into a single test probe. Furthermore, bonding problems in soldered and bonded layers between heat sinks and IC housings can be investigated with this ultrasonic imaging system. It has a high resolution, for example a lateral resolution of approximately 150 micrometers. In addition to these applications in material testing, the ultrasonic imaging system can be used in the field of medicine, for instance, for the diagnosis of the degeneration of the optic nerve in case of glaucoma, in which case an ultrasonic frequency setting of apprioximately 15 MHz is used. Further application in the field of skin diagnosis, and for heart and kidney diagnosis on a patient during surgery for localizing a stenosis or a kidney stone are contemplated. For this purpose, a higher ultrasonic frequency is practical, preferably at least 30 MHz. In addition to the C-image, the device also provides the ultrasonic B-image normally used in medicine.

Other features and advantages of the invention will be apparent from the following description of the preferred embodiments, and from the claims.

For a full understanding of the present invention, reference should now be made to the following detailed description of the preferred embodiments of the invention and to the accompanying drawings.

DETAILED DESCRIPTION

Preferred embodiments of the invention will now be described with reference to the Figs.

Figure 1:
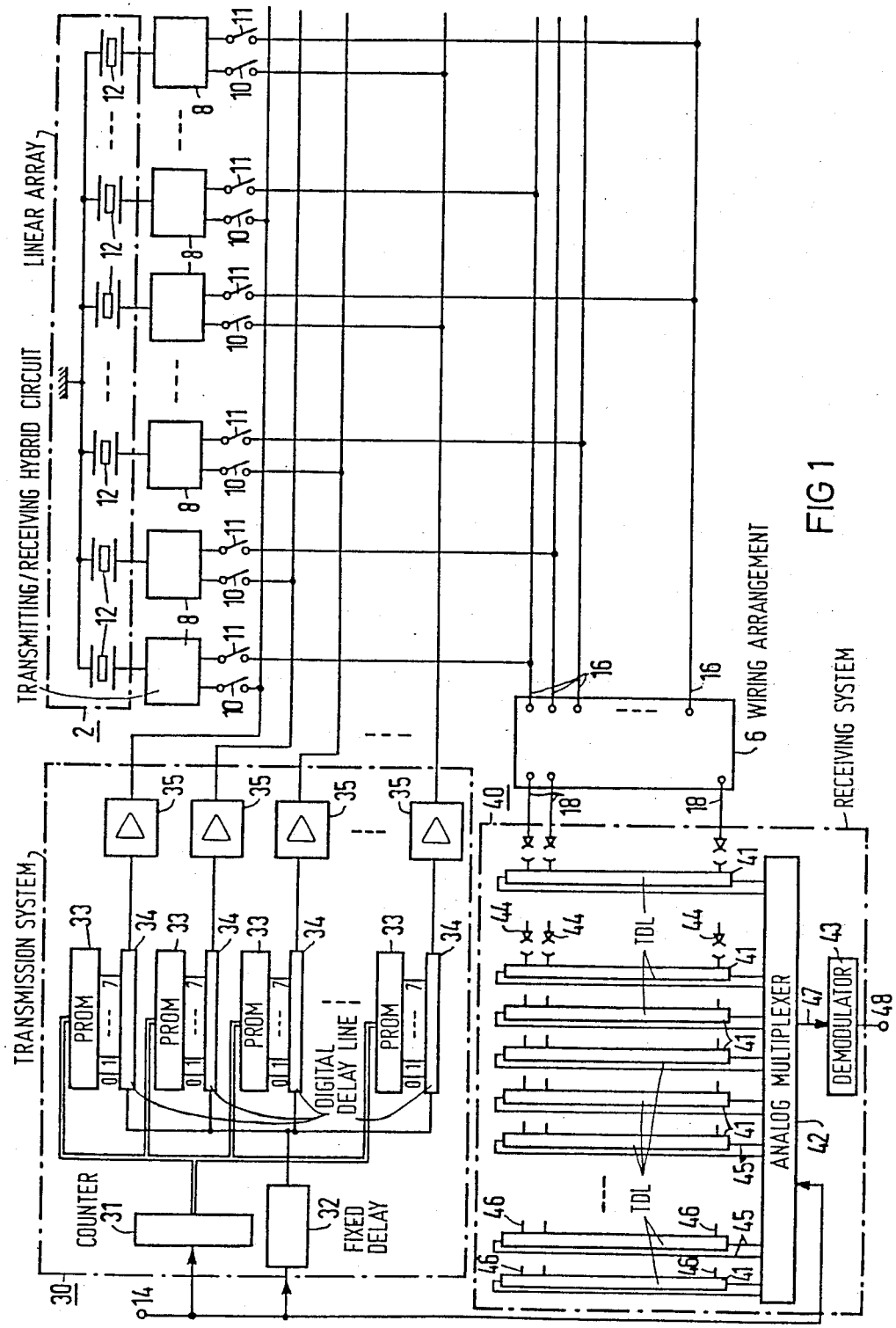
FIG. 1 shows a block diagram of the ultrasonic imaging system.

In FIG. 1, a block diagram of the ultrasonic imaging system is shown which consists of a linear array 2, a transmission system 30, a receiving system 40, a wiring arrangement 6, and of several, typically 300, transmitting and receiving hybrid circuits 8. Furthermore, one transmit switch 10 and one receiver switch 11 are allocated to each of the transmitting and receiving hybrid circuits 8. The linear array contains several, preferably 300 transducer elements 12, which, for instance, may consist of lead-metaniobate $Pb(NO_3)$, preferably lead-circonate-titanate PZT. The ultrasonic frequency of these transducer elements 12 is preferably at least 30 MHz. In this ultrasonic imaging system operating in the pulse-echo mode, only one group each of n (preferably 15 and specifically 30) transducer elements 12 is active at the same time. These n active transducer elements 12 make up the beam aperture, which, for instance, is electronically advanced by means of the group advancement, preferably by using the half-cycle method and specifically by using the modified half-cycle method. The selection for the purpose of focusing takes place through phase-delaying. The grid size of the linear array 2, e.g., consisting of 300 transducer elements 12, is typically 150 micrometers whereby the actual modulation width, which is equal to the grid size minus the width of the cross-section, is approximately 100 micrometers. The entire length of the array 2 measures, therefore, only 45 mm. The length of the modulations for instance, is 5.5 mm, while their thickness is a function of the resonance requirement. For lead-metaniobate $Pb(NO_3)$, the thickness of the transducer elements, for instance is approximately 55 micrometers, and for lead-zirconate-titanate PZT the thickness is approximately 67 micrometers.

The transmitting system consists of a 5-bit counter 31, a fixed delay 32, several programmable read-only memories 33, several digitally programmable delay lines 34 and several transmitting amplifiers 35. One of the PROM's 33, one digital programmable delay line 34 and one transmitting amplifier 35 are allocated to each of the n active transducer elements 12 of the beam aperture if the electronic advancement of the sound field takes place according to the group advancement. The beam aperture, for instance, is made up of 30 transducer elements.

However, if the electronic advancement of the sound field is implemented by the half-cycle method or the modified half-cycle method, the transmitting system 30 is expanded by one channel, i.e., by one PROM 33, one digitally programmable delay line 34, and by one transmitting amplifier 35. Thus the beam aperture consists of alternately n or n+1 active transducer elements 12. The selection of the transmitting amplifiers 35 takes place via square wave pulses which are supplied by a clock pulse generator (not shown in the Fig.) at input 14. These square wave pulses are delayed by means of the programmable delay line 34. The delay times are stored each time in the PROM 33 in digital form. The preferred programmable read-only memories to be provided are PROM's having a memory organization of 32×8 bits. These PROM's are addressed via 5-bit addresses which are generated by means of the 5-bit counter 31.

The receiving system 40 consists of several analog delay lines 41, one analog multiplexer 42, one demodulator 43 and several amplifiers 44 with power terminals. Tapped delay lines TDL's are provided as analog delay lines 41. These delay lines are provided with a tap 45 on both sides, which means that either of the two ends of the tapped delay lines can be used as signal output.

If the electronic advancement of the sound field is accomplished according to the group advancement or according to the modified half-cycle method, the receiving system contains 40 n/2 tapped delay lines (TDL's). However, if the electronic advancement of the sound field takes place using the half-cycle method, the receiving system contains 40 n tapped delay lines TDL's. When the group advancement and the half-cycle method is used, n/2 taps 46 are provided each time for one tapped delay line TDL, and, if the modified half-cycle method is used, n/2+1 taps 46 are provided with two amplifiers 44 with power terminals. The maximum delay time of a tapped delay line TDL is approximately 100 nanoseconds. Each tap 45 of the tapped delay lines TDL's is connected to an analog multiplexer 42, whose output 47 is connected to the demodulator 43. The selection of the analog multiplexer 42 takes place by square-wave pulses, which are supplied by a pulse generator (not shown in the Fig.) at the input 14. The receiving system 40 and the transmitting system 30 are controlled synchronously by a clock pulse generator. A video signal is obtained at the output 48 of the demodulator 43, which is displayed on a viewing screen (not shown in the Fig.).

In the wiring arrangement 6, the signal lines 16, which are connected by means of the receiver switches 11 to a transducer element 12, are wired to the inputs 18 of the receiving system 40.

When using the group advancement, n signal lines 16 are connected to $n/2 \times n/2$ inputs 18 of the receiving system 40. The number of inputs 18 totals $n/2 \times n/2$, because n/2 tapped delay lines TDL's with n/2 taps 46 are available when using the group advancement. If electronic advancement of the sound field by the half-cycle method is used, $n+1$ signal lines 16 are permanently connected to $n \times n/2$ inputs 18, and if the electronic advancement of the sound field takes place using the modified half-cycle method, $n+1$ signal lines 16 are permanently connected to $n/2 \times (n/2+1)$ inputs 18.

However, when using this solution of permanent wiring of signal lines 16 and inputs 18 of the receiving system 40, more delay lines 41 are required than when using a switching matrix as in the present state of the art. Use of a switching matrix could possibly still be implemented for ultrasonic frequencies below 10 MHz, but for ultrasonic frequencies in the order of 30 MHz, for instance, the design of a switching matrix that still functions properly seems practically impossible, primarily due to the negative effects to be expected from electric couplings and because switching matrix networks switches can only be implemented with great difficulty at these high frequencies.

Figure 2:
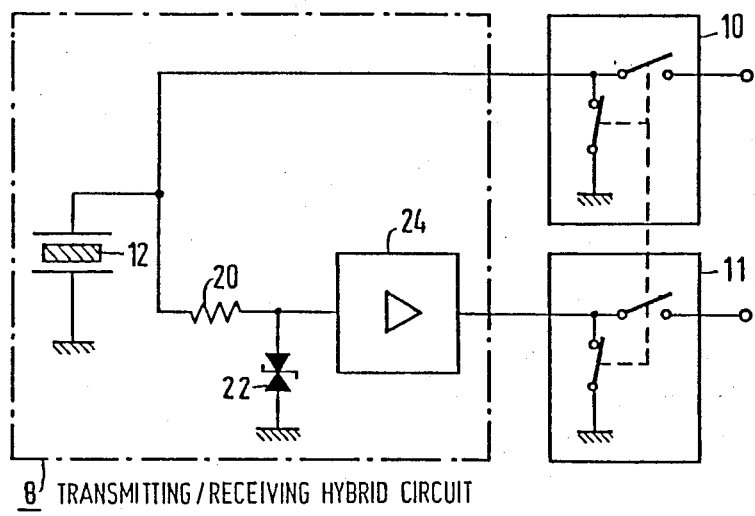
FIG. 2 illustrates an advantageous transmitting and receiving hybrid circuit.

FIG. 2 shows an advantageous transmitting and receiving hybrid circuit 8 with a transmit switch 10 and a receiver switch 11. The purpose of this transmitting and receiving hybrid circuit 8 is to separate the respective transmission and receiving signals of the transducer elements 12.

During transmission the transmit switch 10 is directly coupled to the transducer element 12; during receiving, a resistor 20, a so-called bi-directional transients absorption Zener diode 22 and a reception amplifier 24 are connected between the receiver switch 11 and the transducer element 12. The bidirectional transients absoprtion Zener diode 22 with low threshold voltage serves as protection for the receiver input. The resistor 20 determines the magnitude of current flowing through the bidirectional transients absorption Zener diode 22. Since this transmitting and receiving hybrid circuit 8 does not form a closed circuit, the tendency to oscillate is avoided. These switches 10 and 11 are each implemented as double-pole switches because of the stop-band attenuation that can be achieved in this manner. The switching clicks of transmit switch 10 are practically eliminated if PIN diodes are used as switches 10. During receiving, a CMOS switch is used as receiver switch 11 because of the ease of activation with a TTL level and the high stop-band attenuation.

In order to achieve a relatively long focus in case of a narrow focusing width, the so-called Axicon principle is used. For ultrasonic arrays that operate in accordance with the Axicon principle, the delay time increases linearly from the value zero in the center of the lens up to a maximum value at the perimeter of the active array. When using the group advancement, n transducer elements are connected together into a group for common radiation and receiving and thus form the beam aperture. It produces one line of the ultrasonic image. By periodically switching in a transducer element on one side of the group and simultaneously switching out a transducer element on the opposite side, the image line is shifted by the width of one transducer element. When using the half-cycle method, the consistency of the image presentation can be enhanced by alternately switching a transducer element in and out. By switching a transducer element alternately in and out, the line density can be doubled with the same number of transducer elements.

Figure 3:
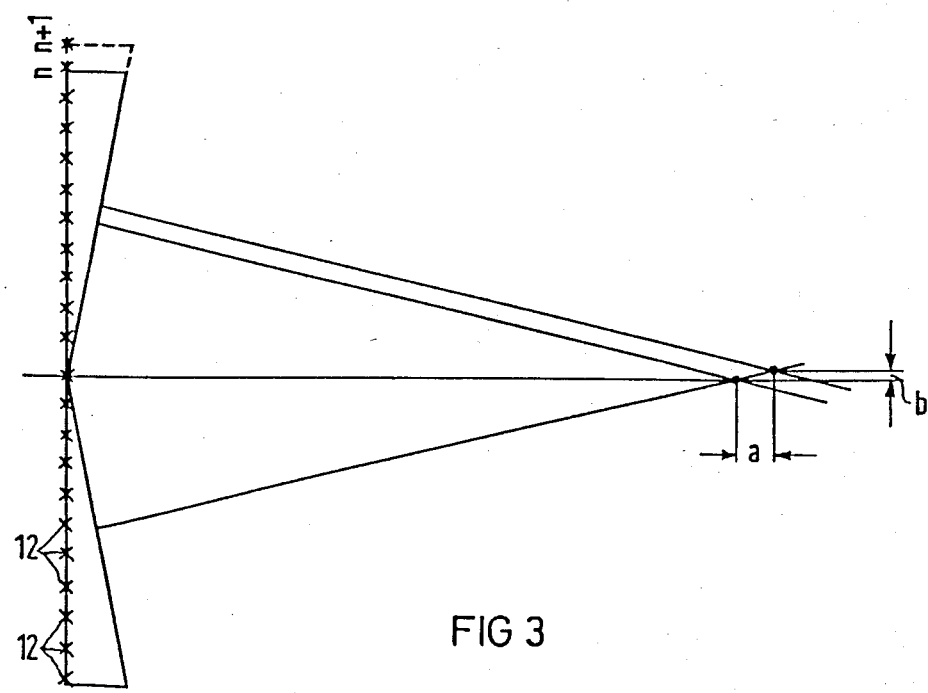
FIG. 3 shows a method of electronic advancement of a sound field.

In FIG. 3, a method for electronic advancement of the sound field is presented. This electronic advancement of the sound field takes place using the modified half-cycle method. The beam aperture in accordance with the advancement pulse consists alternately of n or $n+1$ transducer elements 12. This additional $n+1$ transducer element 12 is attached asymmetrically to the active lens of the n transducer elements. The delay time of the $n+1$ transducer element 12 is greater than the delay time of the nth transducer element 12. The delay times are predetermined by the Axicon principle in accordance with which the delay time increases from zero in the center of the lens up to a maximum value at the perimeter of the active array. Due to this asymmetrical attaching of $n+1$ transducer element 12, the desired lateral shift of the sound field by half the grid dimension "b" is obtained. This is the same as for the half-cycle method. Also associated with this is an increase "a" in the focusing depth of the order of approximately 10% for example, which is the same as for the half-cycle method. However, this increase can be tolerated within the scope of the achievable focusing length, if the utilization of the overall focusing length is limited, for example, to a 1 to 1.5 mm long center-area.

The difference between the half-cycle method and the modified half-cycle method lies in the design of the receiving system 40. By using the modified half-cycle method, the n tapped delay lines TDL's for the half-cycle method are reduced to n/2 tapped delay lines TDL's but, instead of n/2 taps 46, $n/2+1$ taps 46 are now provided on the tapped delay lines TDL's for the time stage being added.

There has thus been shown and described a novel ultrasonic imaging system which fulfills all the objects and advantages sought therefor. Many changes, modification, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. In an ultrasonic imaging system with a linear array having several transducer elements of which a respective group of commonly controlled transducer elements forms a beam aperture and to which one transmitting system and one receiving system are allocated and which are equipped with an electronic focusing of the sound field by phase delay and with parallel scan of the sound field by electronic advancement, the improvement wherein:

(a) said transmitting system comprises for said transducer elements of said beam aperture respectively one digitally programmable delay line, one PROM and one transmitting amplifier;

(b) said receiving system comprises for each of said transducer elements of said beam aperture one, respective analog delay line which is equipped with n/2 taps;

(c) said imaging system comprises a common analog-multiplexer for all of said analog delay lines; and (d) said transducer elements of said linear array are each connected to said transmitting system via a transmit switch and each of said elements is connected via a receiver switch in series with a permanent wiring arrangement to said receiving system.

2. Ultrasonic imaging system in accordance with claim 1, wherein said PROM is a programmable read-only memory with a memory organization of 32×8 bits.

3. Ultrasonic imaging system in accordance with claim 1, wherein said transmitting system further comprises a 5-bit counter.

4. Ultrasonic imaging system in accordance with claim 1, wherein said analog delay lines are tapped delay lines (TDL) of said receiving system.

5. Ultrasonic imaging system in accordance with claim 4, wherein said taps of said tapped delay lines (TDL) are located on both ends of said delay lines.

6. Ultrasonic imaging system in accordance with claim 1, further comprising amplifiers, each two of said amplifiers being coupled to said taps of said analog delay lines, each of said amplifiers including a power terminal.

7. Ultrasonic imaging system in accordance with claim 3, wherein said analog-multiplexer of the receiving system and the 5-bit counter of the transmitting system are connected to a pulse generator.

8. Ultrasonic imaging system in accordance with claim 4, wherein said receiving system includes n/2 of said tapped delay lines (TDL) with n/2 taps each.

9. Ultrasonic imaging system in accordance with claim 4, wherein said receiving system includes n of said tapped delay lines (TDL) with n/2 taps each.

10. Ultrasonic imaging system in accordance with claim 4, wherein said receiving system includes n/2 of said tapped delay lines (TDL) with n2+1 taps each.

* * * * *